United States Patent [19]  
Cocke et al.

[11] 3,966,984  
[45] June 29, 1976

[54] METHOD OF REDUCING AIR POLLUTION BY RECOVERING D-LIMONENE FROM CITRUS PULP PROCESSING OPERATION

[75] Inventors: Emory L. Cocke, Atlanta, Ga.; Fred W. Muncie, deceased, late of Detroit, Mich.; by John W. Muncie, executor, Grosse Pointe Park, Mich.

[73] Assignee: Emory L. Cocke, Atlanta, Ga.

[22] Filed: Nov. 27, 1974

[21] Appl. No.: 527,718

[52] U.S. Cl. ............................ 426/472; 426/486; 426/489; 426/492; 426/616; 426/635
[51] Int. Cl.² .................. A23L 1/00; A23L 2/06
[58] Field of Search .......... 426/472, 478, 486, 489, 426/492, 520, 387, 635, 519, 616

[56] References Cited  
UNITED STATES PATENTS

| | | |
|---|---|---|
| 2,455,782 | 12/1948 | Kuder .......................... 426/489 X |
| 2,525,645 | 10/1950 | Burdick et al. ................ 426/472 X |
| 2,548,510 | 4/1951 | Neal ............................... 426/616 |
| 3,347,681 | 10/1967 | Platt ............................... 426/387 |
| 3,551,163 | 12/1970 | Vincent .......................... 426/616 |
| 3,745,020 | 7/1973 | Lime et al. ..................... 426/519 X |
| 3,763,020 | 10/1973 | Drew et al. .................... 426/492 X |

Primary Examiner—S. Leon Bashore  
Assistant Examiner—Kenneth M. Schor  
Attorney, Agent, or Firm—Beveridge, DeGrandi, Kline & Lunsford

[57] ABSTRACT

In a process of preparing animal feed from citrus residue, the citrus residue is pulverized and pectin is precipitated, preferably with lime. The resulting mixture is then heated to release water and volatile compounds including (d-limonene) from solids. The evaporated water and d-limonene are collected and condensed, thereby preventing their escape into the atmosphere. The solids are then dried in a rotary kiln to yield the animal feed.

7 Claims, 3 Drawing Figures

METHOD OF REDUCING AIR POLLUTION BY RECOVERING D-LIMONENE FROM CITRUS PULP PROCESSING OPERATION

This invention relates to a process of preparing foodstuffs intended for animal use by treating citrus residue, and to the reduction of air pollution by recovering a maximum amount of d-limonene from such a process.

The value of citrus (mainly orange and grapefruit) cannery residue as animal feed has been recognized by various state experiment stations, by dairymen and cattlemen located in the eastern half of the United States and in California and Texas. Because of the high water content and perishable nature of the residue, however, it cannot be transported economically for feeding purposes. The fresh material is difficult to handle, ferments rapidly, and sours, resulting in the attraction of insects, and the emanation of objectionable odors. Its preservation by pressing and ensiling has been reported, but the practice has not been widely adopted.

Processing citrus cannery residue to form a dried citrus pulp is now a widely accepted means of preparing the valuable animal feed. Dried citrus pulp is one of the most digestible ingredients in feed available for cows. When this dried citrus pulp has been fed to dairy herds, milk production has been maintained and animals have been kept in a thrifty condition.

Dried citrus pulp is a citrus cannery residue to which nutrients and other additives can be added, and from which a major amount of liquid has been removed. The citrus residue contains pectin, which binds water in the residue. In the preparation of the dried citrus pulp, the citrus residue is generally limed to destroy the hydrophilic nature of the pectin. The moisture content of the citrus residue is then reduced by draining in bins and/or pressing with auxiliary equipment. The resulting solids or press cake are converted into dried citrus pulp by heating in a rotary kiln (drier) using a direct, hot air or steam tube device.

The liquids from the bins and/or presses are called "peel" liquids, which are comprised of water, carbohydrates, essential oils and d-limonene. It is customary in the citrus by-products industry to recover d-limonene from peel liquids and distillation operations. However, d-limonene in the solids (press cake) is generally carried into the atmosphere with waste gas vapors from the rotary kilns.

d-Limonene is a liquid terpene, $C_{10}H_{16}$, which occurs in citrus fruit. d-Limonene finds use as a solvent, as a wetting and dispersing agent and in the manufacture of resins. Thus, it is desirable to recover this material rather than venting it to the atmosphere. More importantly, it is characterized by an objectionable odor, and is now considered to be an air pollutant. In fact, it is believed that the city of Los Angeles, California, is actively seeking to reduce d-limonene discharges into the atmosphere to tolerable levels.

Up until this invention was made, there was not a satisfactory method of recovering most of the d-limonene from vapors emitted by rotary kilns. The present gas scrubbers, for example, have not been found to be entirely satisfactory in existing plants because of the inefficiency of such equipment and the cost of operation, including breakdowns and normal maintenance shut-downs. A large percentage of d-limonene is now emitted into the atmosphere in vapors from rotary driers (kilns). Furthermore, where new plant construction is contemplated, the installation of these scrubbers is a drawback for reasons of economics. Additionally, such equipment does not recover the escaping d-limonene.

Accordingly, there exists a need in the art for a method of reducing air pollution from citrus pulp processing plants by reducing the quantity of d-limonene in waste gases. The method should permit the recovery of d-limonene for further sale and use. The method should also be capable of being practiced on a large-scale commercial basis with a lower expenditure in plant and equipment than heretofore possible with the more widely practiced methods. Finally, it would be highly desirable if the method could be readily adapted to existing plants by employing much of the equipment already installed, thereby reducing the need for additional costly equipment.

Accordingly, this invention aids in fulfilling these needs in the industry. This invention provides a method of reducing air pollution by recovering d-limonene from citrus residue. The process comprises subjecting to size reduction a citrus residue having a volatilizable component comprising citrus oil, d-limonene, free water and bound water. The citrus residue is then limed to convert a portion of the bound water to free water. The limed citrus residue is heated to a temperature to convert at least a portion of the remaining bound water to free water, and to evaporate at least a portion of the volatilizable component to thereby form a vapor component comprising water, citrus oil and d-limonene. The vapor component is collected and condensed. Preferably, the resulting condensate is separated into a water component and d-limonene (sometimes referred to as "a stripper oil"). This separation is effected by stripper operation well known in the art. The concentrated solids component is dried at an elevated temperature to remove a major portion of residual water, and thereby form a dried citrus pulp. After cooling, the dried citrus pulp is ready for use as an animal feed. The process of this invention can be operated on a batch or continuous basis.

This invention will be more fully understood by reference to the drawings in which.

Figure 1:
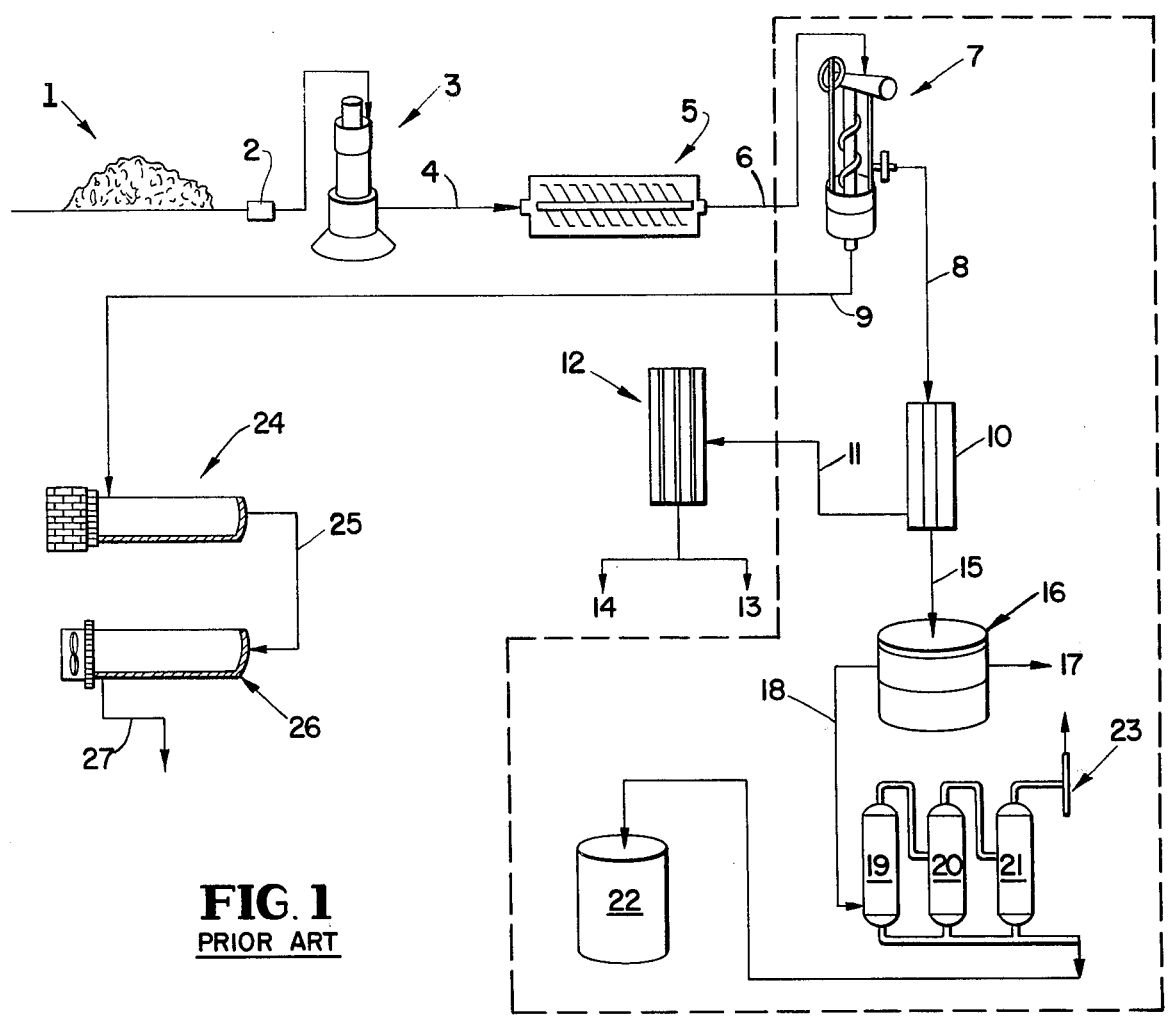
FIG. 1 is a flowsheet of a prior art process.

As used herein, the expression "citrus residue" is to be given a broad meaning. The expression is intended to include the peel, rag, wet pulp, crude fiber and even seeds, if present, remaining after the expression of juice or removal of sections from oranges, grapefruit, limes, lemons and similar citrus fruits. The citrus residue will generally include a substantial quantity of liquids together with smaller quantities of essential oils and d-limonene. In some cases, minor amounts of citrus juice will be entrained in the citrus residue. The amount of liquid, which includes water, oils and d-limonene, in the citrus residue is typically about 80–90 weight percent based on the total weight of the citrus residue. Generally, grapefruit cannery residue contains about 15 weight percent solids and about 85 weight percent liquids. Orange cannery residue usually contains about 80 weight percent liquids, with the remainder being solids. In the heating step, a minimum of about 70 – 75 percent liquid is essential for proper movement of the solids and recovery of the d-limonene as described in detail hereinafter. As a general rule, citrus cannery wastes contain sufficient liquid to render them suitable for use in the process of this invention. Since the object of this invention is the removal of at least a portion of liquids, the addition of water during processing is to be avoided since it increases the energy requirements for dehydration. When a frozen or dried-up residue is employed as a raw material, it may be desirable to add water, but the amount of such residue generally utilized is inconsequential to the total.

Citrus residue is generally comprised of relatively large pieces of peel and agglomerates of rag and pulp. In order to facilitate chemical reaction during the liming of the citrus residue, it is generally desirable to subject the citrus residue to a size reduction operation. This is a conventional operation in the citrus pulp industry. It can be conducted by employing any of the size reduction equipment well known for this purpose. Generally, the equipment is such that the citrus residue is subjected to a slicing, cutting, shredding, chopping, milling, grinding or other subdividing action to reduce the residue to a particle size on the order of about ¼ to about ½ inch in size. Typical devices are hammer mills, shredders, rotary saws, knives, choppers and combinations of these devices.

After size reduction, the citrus residue is limed. Liming destroys the hydrophilic nature of pectin present in the citrus residue, and causes the breakdown of cell walls in the residue. This results in the release of a watery solution comprising water and essential oils, including d-limonene. The watery solution also contains valuable water soluble substances, such as sugars, vitamins and minerals, having significant nutritive value.

Liming involves adding a sufficient amount of calcium oxide or calcium hydroxide to the particles of citrus residue to establish a pH of about 5.5 – 6.5. The amount of lime can vary over a wide range depending upon the characteristics of the citrus residue. Generally, the lime is employed in an amount at least sufficient to coagulate the pectin. Typically, the amount of lime added will be about ⅓ of 1 percent per weight of citrus residue treated. This will typically be about 6 pounds of lime per ton of citrus residue derived from properly ripened fruit in good condition (e.g., not over 3 or 4 percent poor quality fruit). If the fruit has been lowered in quality for any reason, it may be necessary to add additional lime. While chemicals in addition to lime can be added to the citrus residue, lime gives the best results for the economic expenditure.

In a preferred embodiment of this invention, liming is conducted in a delayed conveyor (screw, paddle or ribbon) or pug mill to assure substantially uniform treatment of the citrus residue with the lime. Other equipment which facilitates the intimate contact of the lime and citrus residue can be employed. As persons skilled in the art will recognize, the period of time during which the residue is limed is important, but the time depends upon the quality of the fruit and the size of the particles of citrus residue. Large particles require more time than small particles for lime to penetrate the material. The average time in a delayed screw or pug mill under normal circumstances is about 8 – 12 minutes.

The particles of limed citrus residue are then heated at an elevated temperature to form a vapor component and a concentrated solids component. Heating is conducted at a temperature sufficient to form the vapor component which contains volatiles, including water vapor, essential oils and d-limonene. The heating temperature is typically at least about 225°C, preferably about 225° – 250°C, especially about 225° – 235°C, and at about barometric pressure.

This heating operation to produce the vapor component and concentrated solids component involves the distillation of at least a portion of the volatilizable component in the citrus residue. In order for distillation to be successfully initiated, there must be a sufficient quantity of liquid present. It has been found that it is essential to lime the citrus residue before distillation is attempted. In unlimed, unheated citrus residue, especially peel, most of the water is bound in the cell walls. There is very little free water, and not enough to initiate distillation. This has been found to be the case in present processes in which a large amount of cells in citrus peel, especially the flavedo, are only superficially limed. In the process of this invention, the combined influence of heat and lime ruptures a majority of the liquid-containing cells. Bound liquids are thereby released, and become free liquids in the limed citrus residue. It has been found that these additional free liquids are necessary and sufficient to initiate distillation without the introduction of steam from a secondary source, such as a boiler. Thus, this feature of releasing bound water and distilling it with free water already present in the citrus residue distinguishes the process of this invention from prior art processes in which free water is merely evaporated, and those in which the limed citrus residue is directly contacted with secondary steam. The use of secondary steam is to be avoided since it involves the addition of moisture to limed citrus residue from which one is attempting to remove moisture. Preferably, the bound water is evaporated immediately as it is released from the ruptured cells.

In the heating operation in which the concentrated solids component and vapor component are formed, only a portion of the free water present in the citrus residue is evaporated, but substantially all of the d-limonene and essential oils are carried over into the vapor component. For example, of the total amount of volatilizable component, only about 15 – 50 weight percent is carried over in the vapor component. On the other hand, at least about 75 weight percent, preferably at least about 80 weight percent, of the d-limonene originally present in the citrus residue is carried over into the vapor component.

In a preferred embodiment of this invention, heating of the limed citrus residue to form the vapor component and concentrated solids component is conducted in a heated conveyor provided with agitation means. A preferred device is an enclosed, heated, screw conveyor. The heated screw conveyor can optionally be provided with a hollow shaft for the screw, the hollow shaft enabling the passage of a heating medium therethrough. Further, the screw conveyor can optionally be provided with one or more hollow flights, or hollow paddles, or both. Also suitable are horizontal or vertical cookers equipped with solid or hollow paddles, or hollow flights, or both for conveying the limed citrus residue through the cooker. These devices are preferred since they facilitate the precipitation of calcium salts in and on the limed citrus residue as it gradually progresses through the apparatus.

The vapor component is collected and condensed, thereby preventing the escape into the atmosphere of a substantial portion of the d-limonene originally present in the citrus residue. Conventional condensers, for example, air or water cooled condensers, can be employed for this purpose. The condensate is preferably separated into a water component which can be discarded, and a stripper oil component which comprises at least about 95 weight percent d-limonene, the remainder being a mixture of citrus oils. The d-limonene can be refined if desired.

The concentrated solids component is further processed by drying at an elevated temperature to remove at least a portion of the remaining water. This can be accomplished using conventional equipment, for example, rotary kilns (driers).

Dried citrus pulp is generally considered to be one which has a moisture content of about 5 – 12 percent by weight based on the total weight of the dried citrus pulp. Drying temperatures, residence times in the kilns and kiln construction and operation are well known to persons skilled in the art. Optimum times and temperatures will vary with the equipment employed and can be established with a minimum of experimentation.

The pulp may be cooled after leaving the driers by passing through horizontal or vertical coolers reducing the temperature to approximately that degree which will not cause spontaneous heating when pulp is stored. Temperature and humidity of the atmosphere governs.

A typical prior art process for preparing dried citrus pulp will now be described with reference to FIG. 1. A citrus residue 1 comprising citrus peel, rag and seeds passes under a lime feeder 2 then to a size reduction machine 3, such as a disintegrator. Pulverized, limed citrus residue is discharged at 4, and fed to a delay screw or pug mill 5. Lime 2 is added to the citrus residue to harden sufficiently the pectin to allow subsequent pressing. A portion of the bound liquids contained in the pulverized citrus residue are released by the action of the lime on the cell walls. The larger and firmer pieces, such as the flavedo (rind), react with the lime only on the surfaces of the pieces. They largely retain their shape and cell contents, and consequently are not too absorbent. A conveyor 4 carries limed residue to a pug mill 5.

Limed citrus residue is discharged from mill 5 at 6. It is then fed to a press 7 where a portion of the aqueous liquid is removed. A press liquor 8 and press cake 9 are obtained.

The press liquor 8 is stripped of d-limonene contained therein by steam distillation (also termed steam stripping). This is accomplished by feeding press liquor 8 to a heater 10, which evaporates a portion of the water and citrus oil.

That portion of the press liquor 8 which is not vaporized in heater 10 is discharged from heater 10 at 15, and fed to a settling tank 16 from which sludge 17 is removed. The remaining portion of press liquor 15 is then fed through line 18 to single or multiple effect evaporators such as 19, 20 and 21. The evaporators are capable of producing a product having a solids content of about 72%, in which form the product is sold as citrus molasses 22. In the alternative, the evaporators can produce a molasses product of about 55% solids, which can be combined with press cake 9 for further drying. The pipe for returning 55% molasses to press cake 9 is designated as 23 in FIG. 1.

Press cake 9 is fed to a rotary drier 24 where a substantial portion of the remaining liquids are removed. As used herein, the term "rotary drier" refers to a drier in which the material to be dried is put inside the drier and travels from drier inlet to drier outlet as the drier rotates. A rotary drier is to be contrasted with a drum drier where the material is dried on the outside of the drier. Rotary drier 24 is typically a rotary kiln heated by hot air. Dried citrus pulp is discharged from drier 24 at 25. It is then cooled. While cooling can be accomplished by standing in air at ambient temperature, the use of a cooler, such as 26, is generally more practical in a large scale commercial operation. Cooled, dried citrus pulp is obtained at 27.

When the product from the evaporators is combined with press cake 9 via line 23, drying of the press cake in a hot air rotary drier is a delicate operation if scorching and/or burning of the product is to be avoided. The difficulty is attributable to the molasses from line 23 lying largely on the surface of the superficially limed pieces of citrus residue rather than being absorbed by the pieces.

Some attempt has been made in the past to bypass press 7, and to introduce the limed citrus residue 6 directly into drier 24. This has been found to be impractical, however, due to the tendency of the syrupy limed citrus residue 6 to stick to the surfaces of the drier 24. In addition, removal of water from the system by multiple effect evaporators, such as 19, 20, and 21, is more efficient than attempting to evaporate the same quantity of water in a hot air drier, such as rotary drier 24. Thus, a pressing operation has generally been considered to be essential in the preparation of a high quality dried citrus pulp in large volume.

In prior art processes involving the use of a pressing step, the proportion of liquid removed by pressing may vary. Even when as high a proportion as possible is removed by pressing with the most efficient equipment, only about 50% by weight of the liquids are removed. The liquid removed (press liquor) contains water soluble substances in an amount up to about 12% by weight. The liquid portion remaining in the press cake comprises up to about 65–70% of the cake. Up to about 12% of the liquid portion remaining in the press cake comprises water soluble substances similar to those in the press liquor.

In a pressing operation, citrus oil is removed in about the same proportion as the percentage of press liquor obtained, although the citrus oil is not soluble in the press liquor. Thus, with a removal of only 50% of the total weight as press liquor, and with 70% of the press cake being a liquid similar to press liquor, only 55% of the total citrus oil is removed with the press liquor, while 45% of the citrus oil remains in the press cake. Thus, it is apparent that the pressing step is not very efficient in removing citrus oil even though the step is generally considered to be necessary in the preparation of dried citrus pulp.

The operation of prior art processes similar to that outlined in FIG. 1 is further complicated by the presence of the compound calcium citrate, which is formed by the reaction of citric acid with the lime. While calcium citrate is not appreciably soluble in water, it does not precipitate from cold solutions. Calcium citrate does precipitate, however, when its aqueous solution is heated. Furthermore, calcium citrate does not redissolve when the mixture is cooled. It has been found that calcium citrate precipitates as a sticky solid when the press liquor approaches a temperature of about 145° while being steam distilled for removal of the citrus oil. This sticky solid causes considerable difficulty during the steam distillation operation and the subsequent concentration of the liquor in the evaporators.

The process of this invention overcomes these difficulties by removing the citrus oil from the entire limed citrus residue rather than merely from a press cake fraction. The recovery of d-limonene is thereby increased, and at the same time, the emission of d-limonene from the kilns into the air is greatly reduced. Furthermore, the process of this invention avoids the problems created by the sticky calcium citrate solid during the steam distillation of the press liquor since the calcium citrate is precipitated on and in the fibrous limed citrus residue without precipitation on the inside of processing equipment as is so troublesome at present.

Figure 2:
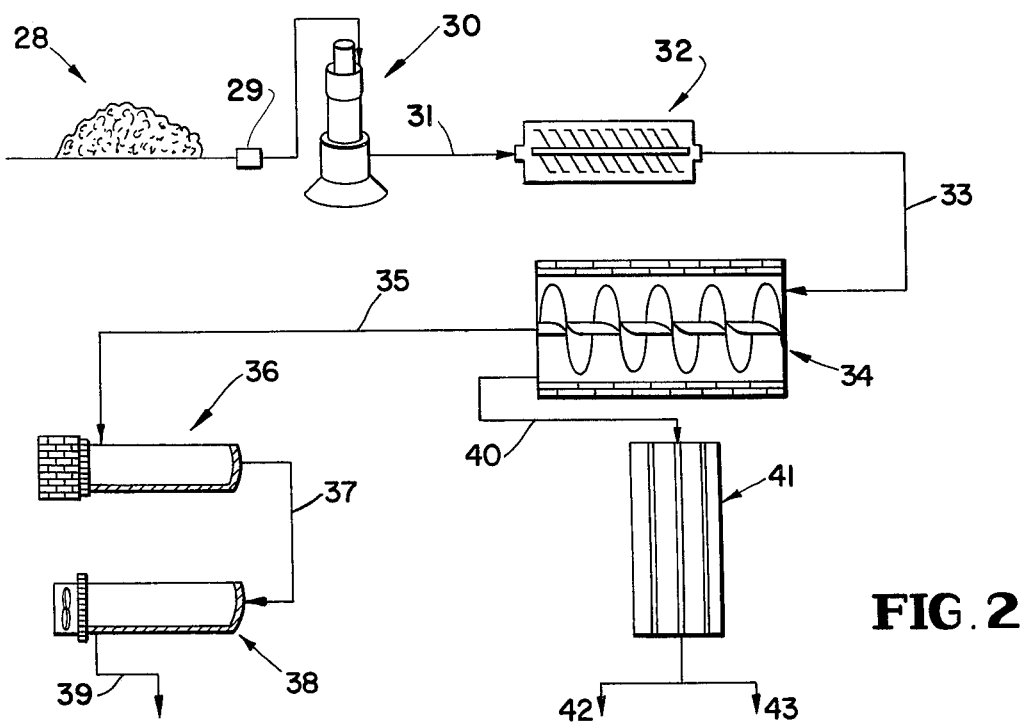
FIGS. 2 and 3 are flowsheets of typical embodiments of this invention. These figures will be discussed in greater detail hereinafter.

Referring to FIG. 2, there is depicted a flow diagram of a typical process according to this invention. Citrus residue 28 comprising peel, rag and seeds passes under a lime feeder 29, then it is conveyed to a size reduction unit in a manner similar to that employed in the prior art. The citrus residue in discharged onto a conveyor 31 and fed into a pug mill 32. The limed citrus residue 33 is then fed into an enclosed, heated, agitating screw, ribbon or cut flight conveyor 34(with or without hollow flights).

It has been found that the combination of heat in the enclosed agitation conveyor 34 and lime in the limed citrus residue 33 disintegrates the cell walls of such firm pieces of material as the flavedo, bleeding out the cell contents and bringing about a marked increase in absorptive capacity of the material. It has also been found that subsequent drying of the concentrated solids component 35 discharged from heated conveyor 34 is greatly accelerated in drier 36. In contrast, prior art processes produce unlimed and only superficially limed chunks of flavedo which present a drying problem.

The vapors from the heated agitating screw conveyor 34 pass into condenser 41 to collect the d-limonene. Vapors usually pass through cyclones, scrubbers or both such devices before being exhausted into the atmosphere.

While removal of d-limonene and the precipitation of calcium citrate might be accomplished by steam distillation of limed residue 33, it has been discovered that bound water released by heating the limed residue in conveyor 34 can be removed readily by heating the citrus residue without the introduction of live steam. Thus, it is essential that the bound aqueous material be bled out of the cells of the citrus residue during heating of the limed residue to provide sufficient moisture to support distillation and evaporation.

The process of this invention also enables the removal of a major portion of the d-limonene present in the citrus residue. The d-limonene is contained in a vapor component 40, which also comprises citrus oil and water. By collecting and condensing the vapor component 40 is a vapor condenser 41, the escape of d-limonene into the atmosphere is prevented. By selectively condensing the substances in vapor component 40, one can obtain stripper oil 42 and water 43. For reasons of safety and economics, condenser 41 is preferably operated at about normal barometric or atmospheric pressure.

The process of this invention not only permits the removal of a major portion of the d-limonene from the limed citrus residue, but the moisture content of the limed citrus residue is so reduced in conveyor 34 that the concentrated solids portion 35 can be introduced directly into a drier, such as 36. Then the dried citrus residue (pulp or meal) 37 passes through cooler 38 and is ready for storage or sale 39.

A comparison of the prior art process depicted in FIG. 1 with the process of this invention set forth in FIG. 2 indicates the simplicity of the method of this invention, as well as the saving in equipment requirements. It is to be expected that processing costs will be similarly reduced. Thus, as will be apparent from the equipment bounded by the dotted lines in FIG. 1, the process of this invention eliminates the conventional pressing operation, stripping of the press liquor of its d-limonene by steam distillation, and evaporation of the press liquor in single or multiple effect evaporators. This is accomplished by the relatively simple step of adding to an existing plant a heated conveyor having agitation means, such as heated screw conveyor 34. The whole of the citrus residue, except the d-limonene, is thereby concentrated in a single product of good marketability and best profit.

Not only are savings in equipment and operating costs achieved by removing a portion of the water by boiling the limed citrus residue, but the character of the fibrous mass and of the dried citrus residue are markedly altered by the substantially complete degradation of the cell walls, and the intimate mixing of the sugars and other water soluble substances with the dried fibers. For example, the absorptive capacity of the dried citrus pulp from the process of this invention is greater than that obtained in some prior art processes. Absorptive capacity refers to the ability of the dried citrus pulp to again take on fluids, such as the digestive fluids in an animal. If the particles are overheated at the beginning of dehydration, the outside of the particle of fruit is hardened (referred to as "case hardening"), thereby reducing the amount of digestive fluid that can reach the inside of the particle.

The dried citrus pulp from this invention contains all of the digestible nutrients of the citrus residue, and therefore is high in digestibles. Since the product of this invention is substantially free of hard and tough pieces of unlimed flavedo, it is especially suitable for pelletizing. The product of this invention is high in NFE (i.e. nitrogen free extract) content, and exhibits desirable absorbent properties. In addition, preservation of the sugars during air drying is more easily achieved with the water soluble substances distributed throughout the limed citrus residue, rather than being largely in a surface layer on the residue as occurs at present when citrus molasses is combined with the only slightly absorbent press cake.

Figure 3:
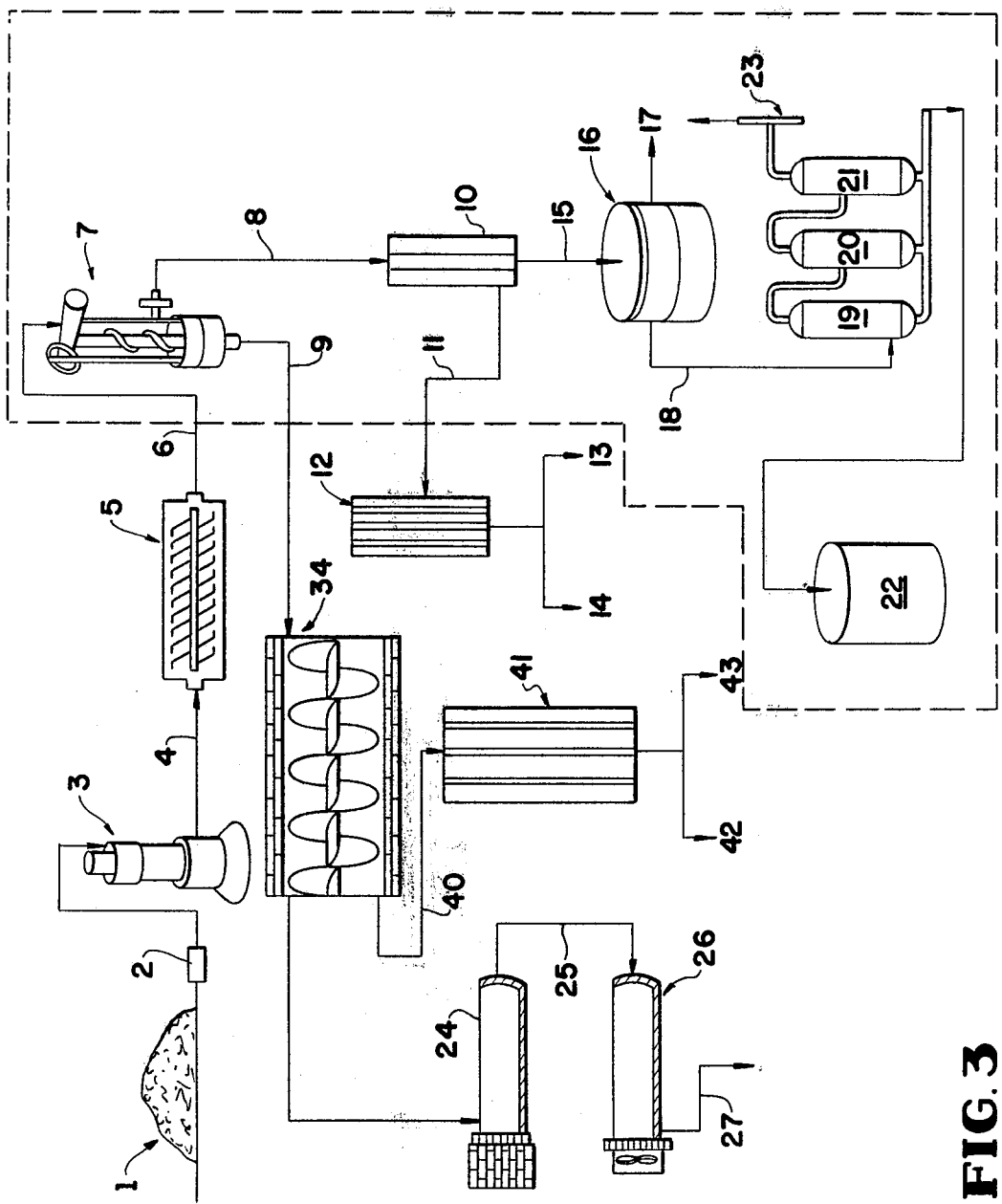

The process of this invention can also be adapted to an existing or new operation in which, for some reason, the use of a press such as 7 is desired (see FIG. 1). FIG. 3 details an installation which provides an optional processing method. Such selection of method will depend upon the cost of fuel and the prices of citrus pulp, meal, molasses and d-limonene.

It is to be understood that conventional nutrients, processing aids and other additives can be added to the citrus residue. For example, molasses and/or molasses containing urea can be conveniently added to the citrus particles (35) before they enter drier 36.

The citrus pulp industry is moving toward pelletizing on a major scale. The advantages of pelletizing are readily apparent when one considers that pellets exhibit densities of about 45 pounds per cubic foot, whereas conventional dried citrus pulp is only about 18

– 20 pounds per cubic foot. Thus, for a given volume, a considerably greater weight of product can be shipped to customers. It is necessary, however, that a material suitable for pelletizing be available. The process of this invention provides such a material.

In order to achieve rapid and uniform removal of water from the limed citrus residue without degradation of the product, a large heating surface per unit weight of citrus residue is desired. Furthermore, in order to achieve the economies and other advantages of a continuous operation, conveying of the citrus residue during heating and agitation is also necessary. These objectives can be achieved readily by the use of a heated conveyor having agitation devices, such as a heated, enclosed, hollow screw conveyor, or one of the other preferred devices hereinbefore described. These devices are capable of providing a large heating area, continuous turnover and forward movement of the citrus residue being processed.

The advantages of this invention will be more fully appreciated from the following Examples in which all parts, proportions, ratios and percentages are by weight unless otherwise indicated.

EXAMPLE 1

A limed, mixed orange and grapefruit residue is subjected to two 10 minute passes through a steam heated, hollow flight screw conveyor. The screw conveyor is a "HOLLO-FLITE" (Tradename) processor having a length of 4 feet – 5 – 19 inches high and inner flights rotatable at 1–25 rpm. The characteristics of the residue before and after passage through the conveyor are set forth in the following table.

| | Weight % Moisture | Weight % d-limo-nene | Steam psi | Moisture Removal as % of total | d-limonene Removal as % of total |
|---|---|---|---|---|---|
| Unheated Residue | 78.6 | 0.43 | 30 | — | — |
| After First Pass | 70.6 | 0.11 | 38 | 27.3 | 74.4 |
| After Second Pass | 60.0 | 0.07 | 40 | 46.5 | 83.7 |

EXAMPLE 2

A citrus residue comprised mainly of grapefruit residue is processed in the same manner as the residue of Example 1. The following results are obtained.

| | Weight % Moisture | Weight % d-limo-nene | Steam psi | Moisture Removal as % of total | d-limonene Removal as % of total |
|---|---|---|---|---|---|
| Unheated Residue | 77.4 | 0.29 | 26 | — | — |
| After First Pass | 69.2 | 0.08 | 28 | 26.7 | 72.4 |
| After Second Pass | 63.8 | 0.06 | 30 | 37.6 | 79.3 |

EXAMPLE 3

The press cake from a conventional citrus pulp processing operation is processed in the same manner as the citrus residue of Example 1. The following results are obtained.

| | Weight % Moisture | Weight % d-limonene | Steam psi | Moisture Removal as % of total | d-Limonene Removal as % of total |
|---|---|---|---|---|---|
| Unheated Residue | 68.8 | 0.31 | 60 | — | — |
| After First Pass | 61.8 | 0.04 | 50 | 18.4 | 87.1 |

Example 3 is included to show that a press cake can be processed according to this invention in order to remove d-limonene.

Inasmuch as the most efficient presses produce a press cake having 65 – 70% moisture from unheated, limed citrus residue, it is apparent from the foregoing Examples that equal or greater efficiency in moisture removal is achieved by the process of this invention.

The reduction of d-limonene from 0.43% to 0.07% (Example 1) results in a retention of 16% of the total, compared to about 45% in the pressing operation employed in prior art processes. Thus, the process of this invention reduces by 79% hydrocarbon emissions from the rotary kiln stack. It is anticipated that the amount of hydrocarbons remaining in stack gases will no longer be considered objectionable.

As used herein, the term "volatilizable component" refers to a substance having several constituents which can be converted from solid or liquid form to a vapor at the temperatures at which the limed citrus residue is heated during the formation of the concentrated solids component.

The term "free water" refers to the water which is released from the citrus residue under pressure. The term "bound water" refers to the water which cannot be expelled by pressure, since it is bound within the pectin.

The process of this invention is accompanied by many advantages. First of all, it substantially reduces air pollution by recovering d-limonene. Secondly, that d-limonene which is recovered is available for further sale or use. The process of this invention may be capable of being practiced on a large scale commercial basis with lower expenditures in plant and equipment than heretofore possible with the more widely practiced method. Also, the process of this invention can be readily adapted to existing plants by employing much of the equipment already installed thereby reducing the need for additional costly equipment. The process of this invention eliminates the need for a pressing step. Also, the process of this invention enables the more complete removal of d-limonene from citrus pulp. Furthermore, calcium citrate formed during the processing operation is precipitated mainly on and in the fibrous limed citrus residue as it progresses through the heated conveyor, and not on and in processing equipment. The calcium citrate which precipitates in tubes of preheaters and evaporators forms a hard mass, which must be reamed or prodded out of the tubes. Chemicals are sometimes used to dissolve the hardened calcium citrate. The expense of such cleaning is greatly reduced or avoided by this invention. The process of this invention results in the substantially complete degradation of the cell walls of the citrus residue, and the intimate mixing of the dried sugars and other water soluble substances with the fibers in the residue. The process of this invention yields a product having desirable physical properties, and one which is high in nutritive value. The product obtained is well adapted for pelletizing. Additionally, the amount of moisture removed from the citrus residue is equal to or greater than the amount removed by prior art processes. The process of this invention eliminates the need for draining liquids from citrus residue in bins and the accompanying loss of valuable soluble nutrients.

What is claimed is:

1. A method of reducing air pollution by recovering d-limonene from a process for the preparation of dried citrus pulp from a citrus residue, said method comprising:
   a. subdividing a citrus residue having a volatilizable component comprising d-limonene, citrus oils, free water and bound water;
   b. liming said citrus residue to convert a portion of the bound water to free water;
   c. heating and agitating said limed residue where said heating is to a temperature sufficient to convert at least a portion of the remaining bound water to free water and to evaporate at least a portion of free water and liquids to thereby form (1) a vapor component comprising water, citrus oil and d-limonene, and (2) a concentrated solids component;
   d. collecting and condensing said vapor component;
   e. drying said concentrated solids component at an elevated temperature to remove a major amount of residual water and thereby form a citrus pulp; and
   f. cooling said citrus pulp.

2. A method according to claim 1 in which liquids condensed from said vapor component are separated into a stripper oil component and a water component.

3. A method according to claim 1 in which said limed citrus residue is heated in a jacketed screw conveyor having a hollow shaft and hollow flights.

4. A method according to claim 1 in which said limed citrus residue is heated in a vertical or horizontal heating device having conveying means.

5. A method according to claim 4 in which said conveying means comprise conveying paddles or flights.

6. A method according to claim 1 in which said method is operated on a continuous basis.

7. A method according to claim 1 in which said limed citrus residue is a press cake.

* * * * *